United States Patent [19]
Preidel

[11] Patent Number: 5,230,786
[45] Date of Patent: Jul. 27, 1993

[54] SILVER-CHLORIDE REFERENCE ELECTRODE

[75] Inventor: Walter Preidel, Erlangen, Fed. Rep. of Germany

[73] Assignee: Siemens Aktiengesellschaft, Munich, Fed. Rep. of Germany

[21] Appl. No.: 691,705

[22] Filed: Apr. 26, 1991

[30] Foreign Application Priority Data

May 2, 1990 [DE] Fed. Rep. of Germany ....... 4014112

[51] Int. Cl.$^5$ ............................................. G01N 27/26
[52] U.S. Cl. ........................................ 204/435; 29/825
[58] Field of Search ........................... 29/825; 204/435

[56] References Cited

U.S. PATENT DOCUMENTS

| | | | |
|---|---|---|---|
| 4,011,861 | 3/1977 | Enger | 128/2.06 |
| 4,507,194 | 3/1985 | Shimomura et al. | 204/435 |
| 4,534,353 | 8/1985 | Potter | 128/635 |
| 4,589,418 | 5/1986 | Gopikanth | 128/635 |
| 4,672,970 | 6/1987 | Uchida et al. | 128/635 |
| 4,908,117 | 3/1990 | Kinlen et al. | 204/435 |
| 5,037,527 | 8/1991 | Hayashi et al. | 204/435 |
| 5,066,383 | 11/1991 | Yamaguchi et al. | 204/435 |

FOREIGN PATENT DOCUMENTS 0304933 8/1988 European Pat. Off. .
2215844A 9/1989 United Kingdom .

OTHER PUBLICATIONS

"Initial Use of a pH Triggered Pacemaker" by L. Cammilli, vol. 12, PACE Jun. 1989, pp. 1000-1007.

"Present State of the pH-Triggered Rate-Responsive Pacemaker" by Cammilli, et al., Jul. 1988, Herzschrittmacher, vol. 8, pp. 149-152.

Cieslak and Delnick, "The Fabrication and Performance of a Ag/AgCl Reference Electrode in Thionyl Chloride Electrolyte." *Journal Electrochmeical Society*, vol. 134, pp. 132-134 (1987).

Primary Examiner—John Niebling
Assistant Examiner—Bruce F. Bell
Attorney, Agent, or Firm—Kenyon & Kenyon

[57] ABSTRACT

In the case of a reference electrode with a layer of silver chloride situated on a silver layer, the amount of silver ordinarily released while in use can be significantly reduced by providing the silver-chloride layer with a layer of water absorbing, ionically conductive material which projects out over the surface of the silver-chloride layer.

7 Claims, 1 Drawing Sheet

SILVER-CHLORIDE REFERENCE ELECTRODE

BACKGROUND OF THE INVENTION

The invention relates to a reference electrode with a layer of silver chloride situated on a silver layer.

Description of Related Art

Reference electrodes are used to measure potentials of other electrodes by quasi combining them with the other electrodes to form an electrochemical cell. The most important reference electrodes are the normal hydrogen electrode, the calomel electrode, and the silver-chloride electrode (Ag/AgCl electrode).

Electrochemical sensors and pacemakers, which are implanted in patients' bodies, require implantable reference electrodes with long-term stability. In this connection, the technical literature only proposes Ag/AgCl electrodes for sensors. When these types of reference electrodes are used, however, one cannot rule out silver poisoning of the body, as a result of the required long implantation period (c.f. *Pacemakers* ["Herzschrittmacher"], volume 8 (1988), pages 149 to 152, as well as *PACE*, volume 12 (1989), pages 1000 to 1007).

The object of the present invention is to develop a reference electrode with a layer of silver chloride situated on a silver layer in such a way that the smallest possible amount of silver is released while in use and, therefore, even when implanted in the body for a long time, there can be no damage caused by the silver.

SUMMARY OF THE INVENTION

In accordance with the invention the silver-chloride layer of the electrode is provided with a layer of water absorbing, ionically conductive material. The layer of water absorbing, ionically conductive material projects out over the surface of the silver-chloride layer.

DETAILED DESCRIPTION OF THE INVENTION

Figure 1:
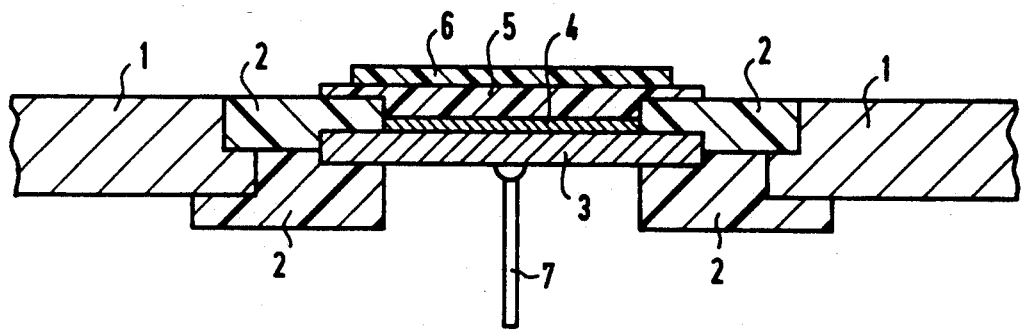
FIG. 1 illustrates a planar reference electrode in accordance with the invention.

Due to its special constitution, the silver-chloride reference electrode according to the invention guarantees that the silver or silver ions are largely prevented from diffusing into the body over a long period of time and are therefore kept below a reasonable value. Tests on laboratory animals have shown that the small quantities of silver that are released are tolerable, because they do not cause any significant increase in silver concentration in the blood.

In the case of the reference electrode according to the invention, the silver-chloride layer is preferably covered with a layer of a poly(perfluoroalkylene)-sulphonic acid, whereby the acid groups are neutralized; nafion is generally used for this. These types of layers, which can be between 1 and 100 um thick, are semipermeable, so that during operation, the required electrical contact is provided between the electrode and the surrounding electrolyte. The layer of water absorbing, ionically conductive material can also be advantageously a thin layer of polyurethane; the thickness of such a layer amounts more or less to 0.1 to 2 um. Mixtures of polyurethane and poly(perfluoroalkylene)-sulphonic acid also come under consideration, for example, as water absorbing, ionically conductive material.

When layers of poly(perfluoroalkylene)-sulphonic acid are used for a long-term implantation, it is advantageous to provide these layers with an insulating film of a body compatible polymer, whereby the polymer film does not completely cover the surface of the layer of poly(perfluoroalkylene)-sulphonic acid. In this manner, the reference electrode only has contact with the surrounding electrolyte through the part of the layer of poly(perfluoroalkylene)-sulphonic acid projecting over the silver-chloride layer and not covered by the polymer film. Thus, there is a diffusion barrier in this case, which—even in the long run—can only be overcome by very small silver quantities. Preferably, epoxy resins, polyurethanes or polyorganosiloxanes, that is silicones, are used as polymers.

The reference electrode according to the invention can find application in the case of electrochemical sensors, particularly oxygen sensors and glucose sensors, and also in the case of physiologically controlled pacemakers. It can thereby be configured either—in a planar form (see FIG. 1), that is in a disk shape—on or in a (metal) housing of an implantable unit or—in the form of a cylindrical electrode (see FIG. 2), that is as a rotationally symmetrical member—on an implantable cable. Incidentally, steam can be used to sterilize reference electrodes according to the invention.

The reference electrode according to the invention is manufactured in a simplified manner, in that a silver-chloride layer is applied to a silver layer or to a sleeve of silver, this can be done by applying molten silver chloride. The silver-chloride layer is then provided with a layer of water absorbing, ionically conductive material, for example in the form of a membrane, which—if necessary—is neutralized. If indicated, that is particularly when poly(perfluoroalkylene)-sulphonic acid is used, an insulating film of a body compatible polymer is also applied to this layer or membrane. In the case of cylindrical design, an expanded tube of appropriate material (for example, a silicone tube) can be slid over the layer or membrane.

The reference electrode is preferably manufactured in the following manner. First the outer surface of a silver layer, which can exist in planar or cylindrical form, is anodically converted into silver chloride, for example with the application of a common salt solution. A solution of a water absorbing, ionically conductive material is then applied to the silver-chloride layer, whose surface can be roughened. In the case of a poly(perfluoroalkylene)-sulphonic acid, for example, this is in the form of a commercial nafion solution (5% solution in isopropanol). After that, the solvent is removed, which takes place for example by drying at a temperature of between 70° and 120° C. When poly(perfluoroalkylene)-sulphonic acid is used, one also subsequently neutralizes, for which generally a common salt solution or Ringer's solution is used; in this case the $SO_3H$ groups are essentially converted into $SO_3Na$ groups. The completeness of the ion exchange can thereby be determined by measuring the potential of the electrode—compared with another Ag/AgCl reference electrode: if possible, it should amount to zero.

If indicated, the layer of ionically conductive material is also provided with a covering layer. For this purpose, a solution of a film-forming body compatible polymer is applied to the layer of the poly(perfluoroalkylene)-sulphonic acid. This can be, for example, an epoxy resin solution or a solution of polyurethane in N-methylpyrrolidone. Afterwards, the solvent is still removed.

The invention shall be clarified in greater detail based on two Examples, in which preferred specific embodiments of the reference electrode according to the invention are depicted.

EXAMPLE 1

FIG. 1 depicts a planar reference electrode in accordance with the invention. The reference numerals signify: 1 housing; 2 seal or insulation; 3 silver layer or sleeve; 4 silver-chloride layer; 5 layer of water absorbing, ionically conductive material, particularly poly(perfluoroalkylene)-sulphonic acid; 6 insulating film or tube; 7 metal wire (for contacting). The assembly of the electrode is as described above.

EXAMPLE 2

Figure 2:
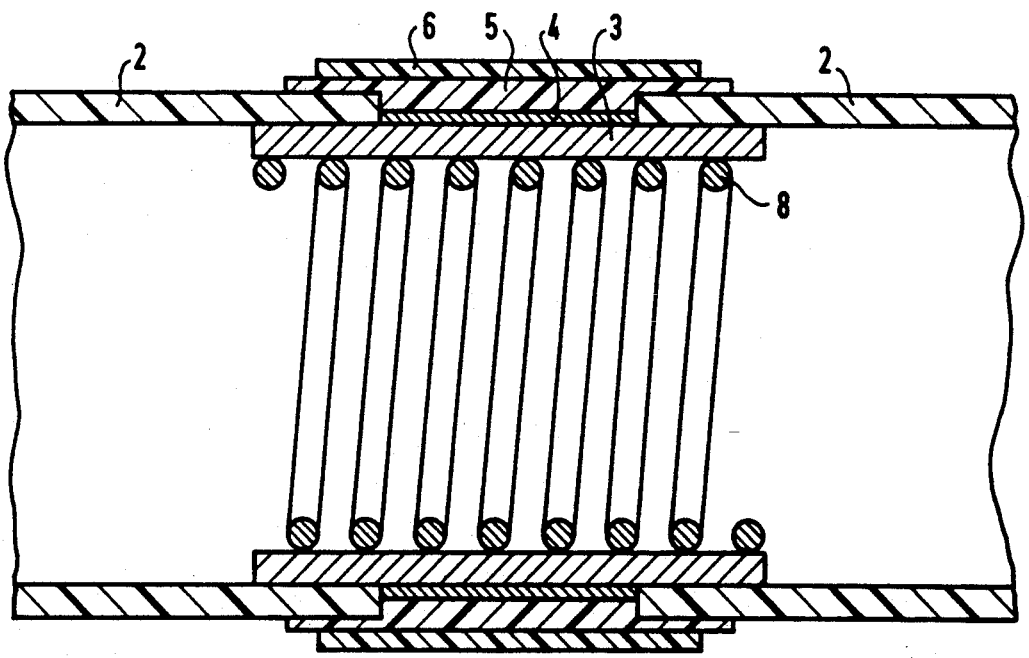
FIG. 2 illustrates a cylindrical reference electrode in accordance with the invention.

FIG. 2 illustrates a cylindrical reference electrode in accordance with the invention. The reference numerals signify the same as in Example 1. Reference numeral 8 designates a metal coil (for contacting).

What is claimed is:

1. A reference electrode consisting of a silver layer, a layer of silver chloride situated on said silver layer, and a layer of water absorbing, ionically conductive material situated on said silver chloride layer and projecting out over the silver chloride layer, said material being selected from the group consisting of polyurethane and poly(perfluoroalkylene)-sulphonic acid, wherein the acid groups are neutralized.

2. The reference electrode according to claim 1, wherein the layer of water absorbing, ionically conductive material is poly(perfluoroalkylene)-sulphonic acid which is provided with an insulating film of a polymer which is body compatible, wherein the polymer film does not completely cover the layer of poly(perfluoroalkylene)-sulphonic acid.

3. The reference electrode according to claim 2, wherein the polymer is selected from the group consisting of epoxy resin, polyurethane and polyorganosiloxane.

4. A method for manufacturing a reference electrode comprising the steps of anodically converting a surface of a silver layer into a silver chloride layer, applying a solution of a water absorbing, ionically conductive material in a solvent to the silver chloride layer, said material being selected from the group consisting of polyurethane and poly(perfluoroalkylene)-sulphonic acid, and removing the solvent to leave a layer of the water absorbing, ionically conductive material.

5. The method according to claim 4 wherein the water absorbing, ionically conductive material is poly(perfluoroalkylene)-sulphonic acid, further comprising the steps of neutralizing the poly(perfluoroalkylene)-sulphonic acid, applying a solution of a film-forming polymer in a second solvent to the layer of the poly(perfluoroalkylene)-sulphonic acid, said film forming polymer being body compatible, and removing the second solvent.

6. The method according to claim 4 wherein the silver chloride layer is roughened.

7. The method according to claim 5 wherein the silver chloride layer is roughened.

* * * * *